United States Patent
Spotorno et al.

(10) Patent No.: US 6,669,734 B2
(45) Date of Patent: Dec. 30, 2003

(54) FEMUR SHAFT PROSTHESIS WITH A PROXIMAL CENTERING APPARATUS

(75) Inventors: Lorenzo Spotorno, Finale Ligure (IT); Werner Güttinger, Winterthur (CH)

(73) Assignee: Sulzer Orthopedics Ltd., Baar (CH)

(*) Notice: Subject to any disclaimer, the term of this patent is extended or adjusted under 35 U.S.C. 154(b) by 244 days.

(21) Appl. No.: 09/976,567

(22) Filed: Oct. 11, 2001

(65) Prior Publication Data

US 2002/0052661 A1 May 2, 2002

(30) Foreign Application Priority Data

Oct. 30, 2000 (EP) .......................................... 00811012

(51) Int. Cl.[7] .................................................. A61F 2/36
(52) U.S. Cl. .................................. 623/23.48; 623/23.15
(58) Field of Search ........................... 623/23.15, 23.19, 623/23.2, 23.21, 23.22, 23.25, 23.46, 23.47, 23.48; 606/95

(56) References Cited

U.S. PATENT DOCUMENTS

| | | |
|---|---|---|
| 4,770,660 A | 9/1988 | Averill |
| 4,938,771 A | 7/1990 | Vecsei et al. |
| 5,766,262 A | 6/1998 | Mikhail |
| 5,885,295 A * | 3/1999 | McDaniel et al. ............ 606/86 |

FOREIGN PATENT DOCUMENTS

| | | |
|---|---|---|
| DE | 19518391 A1 | 11/1996 |
| DE | 19635307 A1 | 3/1998 |
| EP | 0295360 A1 | 12/1988 |
| EP | 0366945 A1 | 5/1990 |
| EP | 0393425 A1 | 10/1990 |
| EP | 0738503 A1 | 10/1996 |
| EP | 0962197 A1 | 12/1999 |
| FR | 2041767 A | 2/1971 |
| FR | 2687306 A1 | 8/1993 |
| GB | 2042897 A | 10/1980 |
| WO | WO 98/17207 A1 | 4/1998 |

* cited by examiner

*Primary Examiner*—David O. Reip
(74) *Attorney, Agent, or Firm*—Townsend and Townsend and Crew, LLP

(57) ABSTRACT

In the figures, proximal centering apparatuses (4) for collar-less femur shaft prosthesis (1) which can be cemented in and which can be pushed from the medial onto the shaft (3) in the cemented region are shown. The centering apparatus (4) has at least in the medial region a centering wedge (6) which widens towards the proximal and which is connected via webs (7) to a clamping apparatus (8), with the clamping apparatus (8) being arranged in the cement-less region of the prosthesis neck (2) and being removable when the webs (7) are interrupted.

10 Claims, 2 Drawing Sheets

Figure 1:
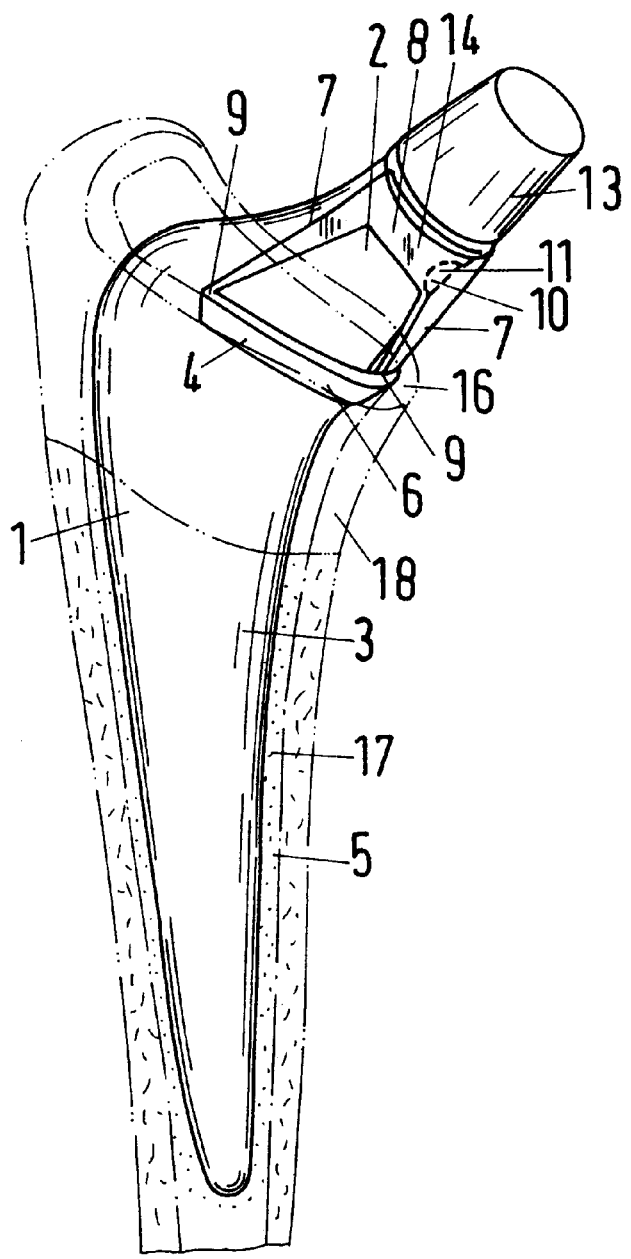

Fig.3
Fig.6
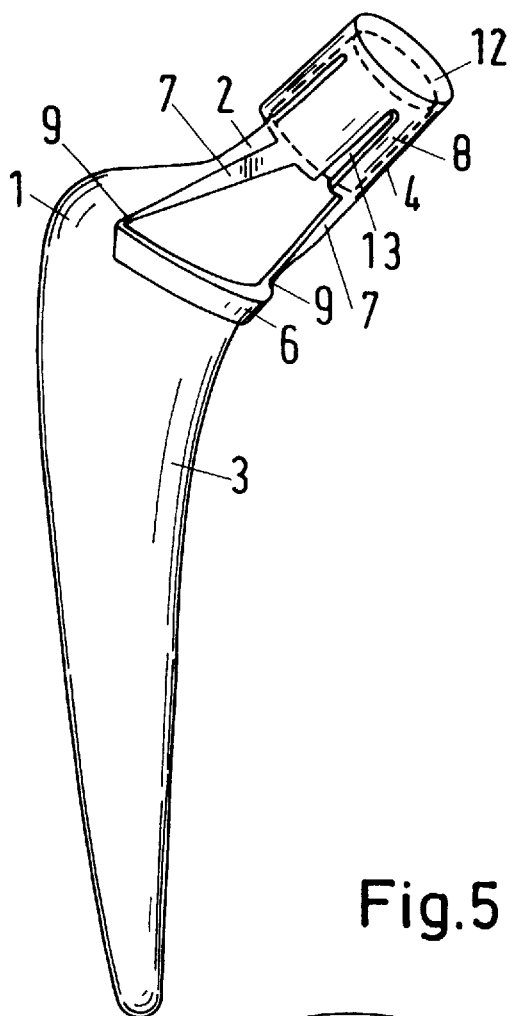
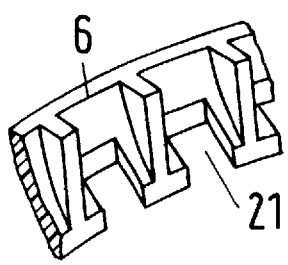
Fig.4
Fig.5
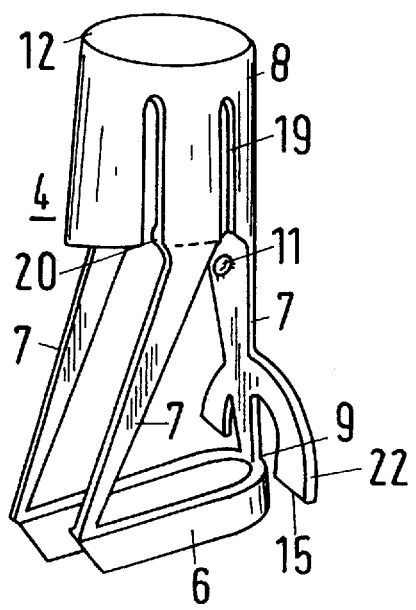
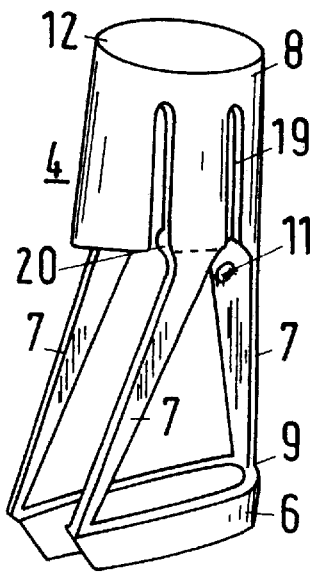

FEMUR SHAFT PROSTHESIS WITH A PROXIMAL CENTERING APPARATUS

The invention relates to a femur shaft prosthesis which can be cemented in and which comprises a prosthesis neck, a shaft and a proximal centering apparatus which can be introduced with the shaft into a bone cavity.

Prosthesis shafts which can be cemented in and onto which proximal centering sleeves can be pushed on from distal are described in the patent application EP-A-0 962 197. These sleeves center the prosthesis shaft in the proximal region in the last phase of its insertion into a bone excavation which is filled up with still flowable bone cement. In a collar-less shaft the exact position along the shaft axis of a sleeve of this kind depends on the cone angle of the shaft in the proximal region and on the diameter tolerances of the sleeve and of the shaft. Prosthesis shafts frequently receive their outer shape through forging, which as a manufacturing procedure has a greater scattering with respect to the shaft diameter. The position of a sleeve which has hopefully been pushed on from the distal end in its correct rotational angular position with respect to the shaft axis fluctuates relatively strongly due to the increasing of the deviations in the axial direction which arise through a weak cone angle. If relatively coarse forging tolerances for the shaft diameter are also present, the axial position of the sleeve with respect to the shaft fluctuates to such an extent that it can no longer be used unconditionally as a height measure for the introduction depth in relation to the resection surface of a tubular bone.

The object of the invention is to create a selectively usable centering apparatus, the axial position of which is independent of the diameter fluctuations of the prosthesis shaft. This object is satisfied in accordance with the independent claim 1 in that the shaft is a collar-less shaft; in that the centering apparatus can be pushed from the medial onto the shaft in the cemented region and has at least in the medial region a centering wedge which widens towards the proximal and which is connected via webs to a clamping apparatus, with the clamping apparatus being arranged in the cement-less region of the prosthesis neck and being removable when the webs are interrupted.

This arrangement has the advantage that it is exactly positioned with respect to the neck region of the shaft, which is usually exactly machined in order for example to fix a ball head, and can thus also be used as a reference for the introduction depth. A further advantage consists in that the centering apparatus does not completely surround the shaft in the cemented region and permits the rising of surplus bone cement. A further advantage consists in that the region in which the centering wedge lies in contact at the shaft in the longitudinal direction can be made short and is limited to pressure zones of the normal loading, whereas in the remaining zones the still liquid bone cement can form a homogeneous, clearance-less pouch.

Subordinate claims 2 to 10 represent further developments of the invention.

Thus the removal of the clamping apparatus after the cementing in is facilitated if the webs have weak points which facilitate a severing or breaking off of the webs. Weak points of this kind advantageously lie at the transition to the centering apparatus in order that no residues project after the removal of the clamping apparatus. If the centering wedge itself consists of bone cement, for example of PMMA, then it can combine with the liquid bone cement at the locations which are wetted by the latter.

An economical manufacture of the centering apparatus results if it is manufactured of a plastic which can be processed on an injection molding machine. Knock out bores or a securing cone at the prosthesis neck are suitable as reference surfaces for the securing of the centering apparatus. An abutment which limits the sinking in of the shaft at the resection surface and which can later be removed can be formed with support surfaces which are anchored at the removable part of the centering apparatus.

Figure 2:
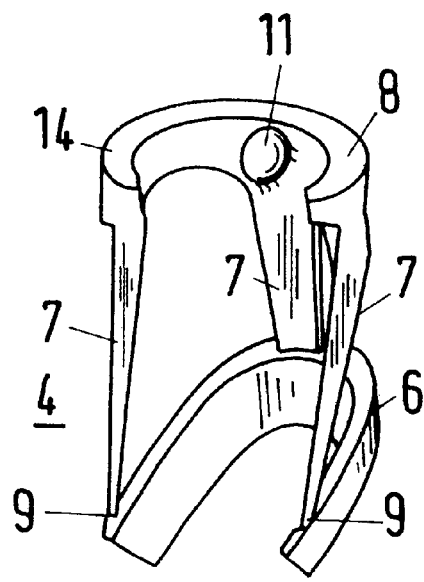

The invention will be explained in the following with reference to exemplary embodiments. Shown are:

FIG. 1 schematically, a shaft with a centering apparatus which is moved in into a bone cavity of a femur bone which is filled with bone cement;

FIG. 2 schematically, an enlarged view of the centering apparatus of FIG. 1;

FIG. 3 schematically, a view of a further embodiment for a centering apparatus which is placed onto a shaft;

FIG. 4 schematically, an enlarged view of the centering apparatus of FIG. 3;

FIG. 5 schematically, a centering apparatus of FIG. 3 in which support surfaces are additionally provided as abutments for a resection surface; and FIG. 6 schematically, an enlarged section of a centering wedge which can be largely wetted with liquid bone cement on the side towards the shaft.

Proximal centering apparatuses for collar-less femur shaft prosthesis which can be cemented in and which can be pushed on from the medial onto the shaft in the cemented region are shown in the figures. The centering apparatus has at least in the medial region a centering wedge which widens towards the proximal and which is connected via webs to a clamping apparatus, with the clamping apparatus being arranged in the cement-less region of the prosthesis neck and being removable when the webs are interrupted.

In the following examples identical reference symbols are used for identical functions.

In FIGS. 1 and 2 a centering apparatus 4 consists of a C-shaped centering wedge 6 which can be pushed on from the medial and which widens towards the proximal and of a clamping apparatus 8 which is connected thereto via webs 7. Three webs 7, of which one extends medially, one posteriorly and one anteriorly, form a stable tripod with a C-shaped ring segment 14. This ring segment 14 surrounds as a clamping apparatus 8 the prosthesis neck 2 over more than 180° and can be spread apart elastically, so that it surrounds the prosthesis neck 2 under a bias stress. The ring segment 14 has medially an inwardly projecting projection 11 which can be anchored in a knock out bore 10 of the prosthesis neck 2. The webs 7 are kept relatively thin in order to obscure as little of the view of the prosthesis as possible. They form a weak point 9 at the transition to the centering wedge 6 which can be easily severed by a scalpel or through engaging behind the webs 7 with a pointed object for breaking.

In accordance with FIG. 1 the femur shaft prosthesis 1 with the centering apparatus 4 placed on can be inserted into a bone cavity 5 of a femur bone 18 which is filled up with bone cement 17. The femur bone 18 has a resection surface 16, up to which the shaft 3 and the centering wedge 6 which lies in contact with it dip in with its upper edge and displace bone cement 17, which is brushed off outside the bone cavity 5. The prosthesis neck ends in a cone 13 which can likewise be used as an abutment surface for the ring segment 14.

In further embodiments in accordance with FIGS. 3, 4 and 5 the cone 13 is completely surrounded by a resilient, slit cap 12 which is connected via three webs 7 to the centering wedge. The centering apparatus 4 is pushed on onto the prosthesis 1 from the proximal-medial, with the cap 12 moving open resiliently and clamping firmly onto the cone surface 13 with inwardly projecting bulges 20, which project beyond the cone 13.

In accordance with FIG. 3 the centering wedge 6 extends from the medial towards the anterior and posterior and is held medially in each case at its anterior and posterior end by a web 7 which enlarges in its cross-section in the direction towards cap 12. The cap 12 is provided with incisions 19 in the longitudinal direction which enable a resilient moving open of the jacket surface and a clamping firmly on the cone 13. A supporting at a suitable bore in the prosthesis neck 2 can be carried out with a projection 11 at the medial web 7. The cap 12 also has the advantage that it protects the surface of the cone 13 against damage, since it is removed only directly prior to the placing on of a femur ball. The centering apparatus 4 with the cap 12 pre-mounted can thus be used at the same time as a protection for the cone 13.

In FIG. 5 two outwardly protruding arms 22 which can be supported with support surfaces 15 on a resection surface and can form in this manner a depth abutment are attached to the medial web 7. The further embodiment is as is described with reference to FIG. 4.

In FIG. 6 a centering wedge 6 is provided on its inner side with recesses 21 which extend from the distal to the proximal. With this the centering wedge 6 can also be wetted on its inner side by liquid bone cement and can form a combination with the shaft 3.

What is claimed is:

1. Femur shaft prosthesis (1) which can be cemented in and which comprises a prosthesis neck (2), a shaft (3) and a proximal centering apparatus (4) which can be introduced with the shaft (3) into a bone cavity (5), characterized in that the shaft (3) is a collar-less shaft; in that the centering apparatus (4) can be pushed from the medial onto the shaft in the cemented region and has at least in the medial region a centering wedge (6) which widens towards the proximal and which is connected via webs (7) to a clamping apparatus (8), with the clamping apparatus (8) being arranged in the cement-less region of the prosthesis neck (2) and being removable when the webs (7) are interrupted.

2. Femur shaft prosthesis in accordance with claim 1, characterized in that the webs (7) have weak points (9) which enable a severing or a breaking off of the webs (7) after the cementing in of the shaft (3) and the centering wedge (6).

3. Femur shaft prosthesis in accordance with claim 2, characterized in that the weak points (9) adjoin directly at the centering wedge (6) in the proximal direction.

4. Femur shaft prosthesis in accordance with claim 2, characterized in that the removable part of the centering apparatus (4) has support surfaces (15) in order to be able to limit the sinking in of the shaft (3) with the resection surface (16).

5. Femur shaft prosthesis in accordance with claim 2, characterized in that the centering wedge (6) has recesses (21) in the direction towards the shaft in order that liquid bone cement can flow in between the centering wedge (6) and the shaft (3).

6. Femur shaft prosthesis in accordance with claim 1, characterized in that the centering wedge (6) consists of bone cement, for example of PMMA.

7. Femur shaft prosthesis in accordance with claim 1, characterized in that the centering apparatus (4) is manufactured of plastic as an injection molded part.

8. Femur shaft prosthesis in accordance with claim 1, characterized in that the prosthesis neck (2) has a knock out bore (10) and the centering apparatus (4) is supported with a projection (11) in the knock out bore (10).

9. Femur shaft prosthesis in accordance with claim 1, characterized in that the clamping apparatus (8) consists of an elastic cap (12) which is supported on a cone (13) of the prosthesis neck (2).

10. Femur shaft prosthesis in accordance with claim 1, characterized in that the clamping apparatus (8) consists of an elastic ring segment (14) which is supported on the prosthesis neck (2).

* * * * *